US008585096B2

(12) United States Patent
Schnell et al.

(10) Patent No.: US 8,585,096 B2
(45) Date of Patent: Nov. 19, 2013

(54) FLUID LINE SAFETY DEVICE

(75) Inventors: William J. Schnell, Libertyville, IL (US); James M. Brugger, Newburyport, MA (US)

(73) Assignee: NxStage Medical, Inc., Lawrence, MA (US)

( * ) Notice: Subject to any disclaimer, the term of this patent is extended or adjusted under 35 U.S.C. 154(b) by 0 days.

(21) Appl. No.: 13/503,734

(22) PCT Filed: Oct. 26, 2010

(86) PCT No.: PCT/US2010/054112
§ 371 (c)(1),
(2), (4) Date: Apr. 24, 2012

(87) PCT Pub. No.: WO2011/056582
PCT Pub. Date: May 12, 2011

(65) Prior Publication Data
US 2012/0214337 A1 Aug. 23, 2012

Related U.S. Application Data

(60) Provisional application No. 61/255,453, filed on Oct. 27, 2009, provisional application No. 61/316,503, filed on Mar. 23, 2010.

(51) Int. Cl.
*F16L 13/04* (2006.01)
(52) U.S. Cl.
USPC ............. 285/92; 285/114; 604/905; 604/533
(58) Field of Classification Search
USPC ............. 285/92, 81, 305, 114; 604/905, 241, 604/533
See application file for complete search history.

(56) References Cited

U.S. PATENT DOCUMENTS

| 3,340,704 A | 9/1967 | Seckerson |
| 3,768,476 A | 10/1973 | Raitto |
| 3,874,713 A | 4/1975 | Myers |
| 3,881,753 A | 5/1975 | Bochory |
| 4,045,058 A | 8/1977 | Eross |
| 4,068,870 A | 1/1978 | Whitney et al. |
| 4,224,937 A | 9/1980 | Gordon |
| 4,230,109 A | 10/1980 | Geiss |
| 4,270,778 A | 6/1981 | Brownell |
| 4,340,052 A | 7/1982 | Dennehey et al. |
| 4,452,473 A | 6/1984 | Ruschke |
| 4,639,019 A | 1/1987 | Mittleman |
| 4,641,646 A | 2/1987 | Schultz et al. |
| 4,785,858 A | 11/1988 | Valentini et al. |
| 4,826,486 A | 5/1989 | Palsrok et al. |
| 4,834,706 A | 5/1989 | Beck et al. |
| 4,950,255 A | 8/1990 | Brown et al. |
| 4,997,421 A | 3/1991 | Palsrok et al. |
| 5,053,015 A | 10/1991 | Gross |
| 5,139,289 A | 8/1992 | Koss |

(Continued)

*Primary Examiner* — David E Bochna
(74) *Attorney, Agent, or Firm* — Miles & Stockbridge P.C.; Mark A. Catan

(57) ABSTRACT

A restraining device for a tubing connector assembly can include a resilient member having a generally U-shape with forked ends that curve toward each other. Each forked end can have a recess between tines thereof. Each recess can have a blind end. The resilient member can have a bend provided with an engagement bump. The engagement bump and forked ends can be aligned such that the engagement bump coincides with a line joining the blind ends. When a cylindrical connector assembly tube is placed in the recesses, the engagement bump is urged against a side of the connector assembly to thereby prevent inadvertent disconnection.

9 Claims, 6 Drawing Sheets

(56) References Cited

U.S. PATENT DOCUMENTS

| | | |
|---|---|---|
| 5,188,398 A | 2/1993 | Parimore et al. |
| 5,248,306 A | 9/1993 | Clark et al. |
| 5,350,201 A | 9/1994 | Bynum |
| 5,362,111 A | 11/1994 | Harbin |
| 5,423,775 A | 6/1995 | Cannon |
| 5,437,648 A | 8/1995 | Graves et al. |
| 5,490,693 A | 2/1996 | Fisher et al. |
| 5,620,427 A | 4/1997 | Werschmidt et al. |
| 5,957,894 A | 9/1999 | Kerwin et al. |
| 5,984,373 A | 11/1999 | Fitoussi et al. |
| 6,076,424 A | 6/2000 | McMurtrey et al. |
| 6,213,996 B1 | 4/2001 | Jepson et al. |
| 6,217,564 B1 | 4/2001 | Peters et al. |
| 6,220,859 B1 | 4/2001 | Hoffman |
| 6,267,754 B1 | 7/2001 | Peters |
| 6,375,231 B1 | 4/2002 | Picha et al. |
| 6,508,807 B1 | 1/2003 | Peters |
| 6,579,253 B1 | 6/2003 | Burbank et al. |
| 6,722,705 B2 | 4/2004 | Korkor |
| 6,893,056 B2 | 5/2005 | Guala |
| 7,156,424 B2 | 1/2007 | McCord |
| 7,347,458 B2 | 3/2008 | Rome et al. |
| 7,390,028 B2 | 6/2008 | Blazek |
| 7,614,123 B2 | 11/2009 | Schweikert |
| 7,744,572 B2 | 6/2010 | Bierman |
| 7,758,082 B2 | 7/2010 | Weigel et al. |
| 8,042,838 B2 | 10/2011 | Buckler et al. |
| 2008/0129042 A1 | 6/2008 | Weigel et al. |

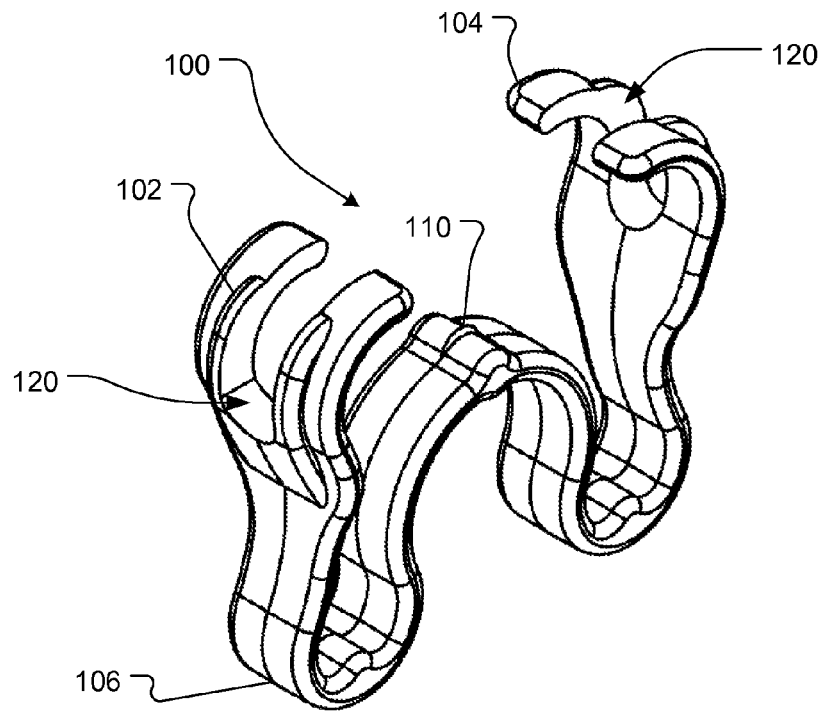
FIG. 3
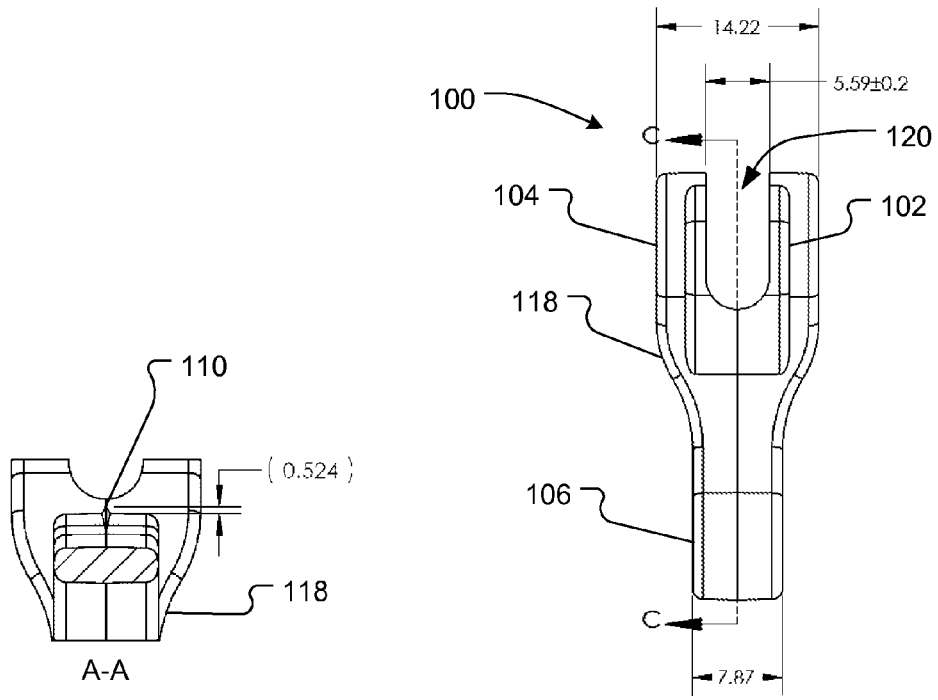
FIG. 4     FIG. 5

FLUID LINE SAFETY DEVICE

CROSS-REFERENCE TO RELATED APPLICATIONS

The present application is a U.S. national stage of International Application No. PCT/US10/54112, filed Oct. 26, 2010, which claims the benefit of U.S. Provisional Application No. 61/255,453, filed Oct. 27, 2009, and U.S. Provisional Application No. 61/316,503, filed Mar. 23, 2010, all of which are hereby incorporated by reference herein in their entireties.

FIELD

This present disclosure relates generally to fluid line connections, and, more particularly, to restraining and safety devices for fluid lines and tubing connections, such as those employed in medical treatment devices.

BACKGROUND

Tubing connections are commonly used in medical treatment systems, chemical processing plants, pharmaceutical plants, laboratories, manufacturing systems, hydraulic systems, etc. A common class of connectors mates by mutually rotating parts of the connectors and/or by pushing the connectors together. A common type of connector is a luer-type connector, which can include a relatively long male element that fits tightly into a channel of a female element.

Originally, luer-type connectors were merely pushed together in order to make a connection. Over time, the connectors evolved to include threaded collars so as to make it more difficult for the connections to arbitrarily disconnect. The threaded collars thus may increase the reliability of the luer-type connections. However, in some applications (e.g., extracorporeal blood treatment systems), it may be desirable to mitigate even minute levels of risk that may be caused by disconnection of the luer-type connections. Accordingly, there is a need in the art for simple and inexpensive ways to increase the reliability of connectors for fluid-carrying vessels. In particular, such a need is felt in the area of tubing systems used in medical treatment devices. It may also be desirable to enhance the security of luer-type connectors without altering the familiar features of their design or usability.

SUMMARY

Various restraining mechanisms and methods for preventing the accidental decoupling of connectors are disclosed herein. A generally U-shaped resilient member can have ends with openings therein for receiving tubing attached to the connectors. The ends of the resilient member can be arranged so as to apply an urging force to opposite ends of the connectors to prevent separation of the connectors. Other portions of the resilient member, such as a centrally located bend with an engagement bump, can interact with a portion of the connectors to further prevent inadvertent connector separation. The various mechanisms and methods are particularly applicable to luer-type connectors. However, the mechanisms and methods can also be used with other types of connectors or connections according to one or more contemplated embodiments.

In embodiments, a restraining device can include a resilient member having a generally U-shape with forked ends that curve toward each other. Each forked end can have a recess between tines thereof. Each recess can have a blind end. The resilient member can have a bend provided with an engagement bump. The engagement bump and forked ends can be aligned such that the engagement bump coincides with a line joining the blind ends. When a cylindrical connector assembly tube is placed in the recesses, the engagement bump is urged against a side of the connector assembly.

In embodiments, a restraining member for a connector assembly can include a forked first end having a first recess between tines thereof and a closed second end having an opening therein. The first recess can be sized and shaped so as to accept a first tubing connected to one end of the connector assembly. The second end can be sized and shaped so as to accept a second tubing connected to another end of the connector assembly. The restraining member can have a bend with an engagement bump arranged between the first and second ends. The bend can be arranged such that, when the first and second ends abut against respective first and second ends of the connector assembly, the engagement bump interacts with a knurled attachment member so as to inhibit rotation thereof.

In embodiments, a tubing set can include a restraining member, a tubing line, and a connector. The restraining member can include a forked first end having a first recess between tines thereof, a closed second end having an opening therein, and a bend with an engagement bump arranged between the first and second ends. The tubing line can pass through the opening in the closed second end of the restraining member. The connector can be attached to an end of the tubing line.

In embodiments, a restraining member for a connector assembly can include first and second ends with a bridge connecting the first and second ends. The first end can have a first U-shaped recess therein. The first recess can be sized and shaped so as to accept a first tubing connected to one end of the connector assembly. The second end can have an opening therein. The second end can be sized and shaped so as to accept a second tubing connected to an other end of the connector assembly. The bridge can have a bend therein with an engagement bump. The restraining member can also have an attachment portion configured to secure the restraining member to the second tubing such that the restraining member cannot be used with another second tubing.

In embodiments, a connector assembly for first and second tubes can have mating connectors thereon. One of the mating connectors can have a locking collar that locks the other of the mating connectors. A restraining member for the connector assembly can include first and second ends and a flexible bridge portion. The first and second ends can be shaped to capture and position first and second mating connector parts attached to the first and second tubes, respectively. The flexible bridge portion can connect the first and second ends. The flexible bridge portion can be shaped such that when the first and second mating connector parts are connected, the first and second ends are urged together thereby urging the first and second mating connectors together. The flexible bridge portion can have an engagement element with an edge that captures and immobilizes the locking collar.

In embodiments, a restraining device can include a resilient member having a generally U-shape with forked ends that curve toward each other. Each forked end can have a recess between tines thereof. The forked ends can have facing bowl shapes. The resilient member can have a bend provided with an engagement bump. The engagement bump and the forked ends can be aligned such that the engagement bump coincides with a line joining the facing bowl shapes. When a cylindrical connector assembly tube is placed in the recesses, the engagement bump is urged against a side of the connector assembly.

In embodiments, a device is configured to urge mating connectors together while simultaneously urging an engagement member into at least one of the mating connectors, such that, by the urging an engagement member, the at least one of the mating connectors is prevented from rotating.

Objects and advantages of embodiments of the present disclosure will become apparent from the following description when considered in conjunction with the accompanying drawings.

BRIEF DESCRIPTION OF DRAWINGS

Embodiments will hereinafter be described with reference to the accompanying drawings, wherein like reference numerals represent like elements. The accompanying drawings have not necessarily been drawn to scale. Any dimensions illustrated in the accompanying graphs and figures are for illustration purposes only and may not represent actual or preferred dimensions. Where applicable, some features may not be illustrated to assist in the description of underlying features.

FIG. 3 is an oblique projection of the restraining clip of FIG. 1.

FIG. 4 is a fragmentary section view A-A of the restraining clip of FIG. 1 taken along plane perpendicular to the view of FIG. 1.

FIG. 5 is an end elevation view of the restraining clip of FIG. 1.

DETAILED DESCRIPTION

Various mechanisms and methods for preventing the accidental decoupling of connectors are disclosed herein. In embodiments, a restraining member to prevent disconnection can apply a biasing force against opposite ends of the connector assembly, thereby urging the connectors together and against separation. The restraining member may include openings and/or recesses through which tubing lines connected to the connector assembly may pass. In embodiments, additional anti-separation components may also be provided in the restraining member. For example, the restraining member may include a protrusion, recess, or other appropriately arranged portion to interact with a portion of the connector assembly, e.g., a rotatable portion of the connector assembly to prevent rotation thereof.

In FIGS. 1-8, an embodiment of a restraining member for a tubing connector assembly is shown. A monolithic member forms a restraining clip 100, which can serve as a fluid line safety device for inhibiting inadvertent disconnection of a connector assembly. The restraining clip 100 can have an undulating shape with curved forked ends 104 and a slot or recess 120 between the tines of the forked ends. The restraining clip 100 may be formed of a resilient material, such as a polymer. However, other materials for restraining clip 100 are also possible according to one or more contemplated embodiments.

Figure 7:
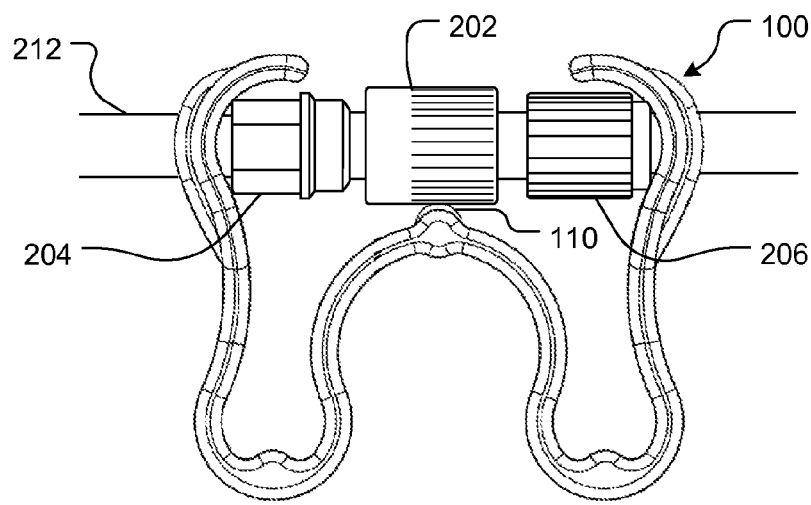
FIG. 7 shows the restraining clip of FIG. 1 attached to interconnected tubing ends according to embodiments of the disclosed subject matter.
Figure 8:
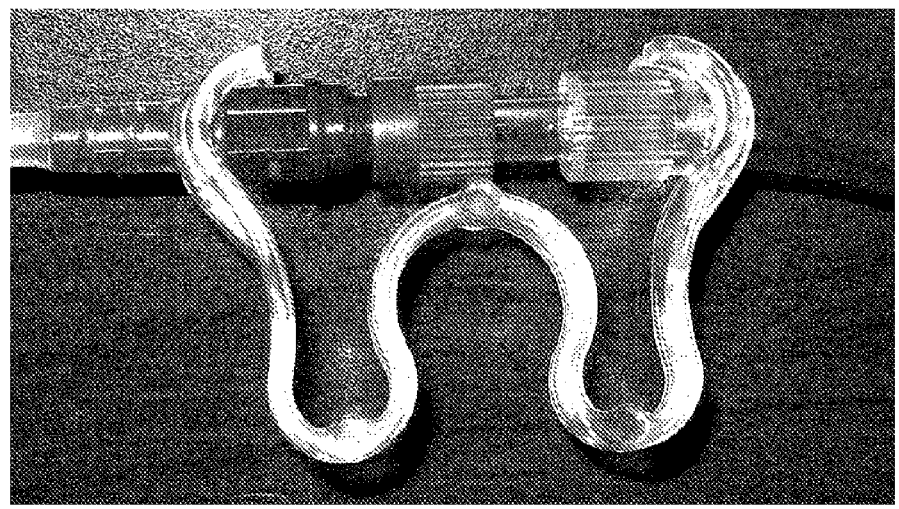
FIG. 8 is an image of an actual embodiment similar to that of FIG. 7.

The shape of the forked ends 104 permits the restraining clip 100 to accommodate the ends of interconnected tube segments, as illustrated in FIGS. 7-8. The forked ends 104 may be connected together by an undulating bridge, which includes an inwardly arching portion 114. The inwardly arching portion 114 has a knife edge bump 110 that engages a knurled attachment member 202 of the connection assembly. The interaction between the bump 110 and the attachment member 202 may prevent, or at least inhibit, it from rotating. A reinforcement bulge 102 ensures that the forked end 104 maintains a curved shape such that the forked ends 104 pushes against the connector ends 204 and 206 while maintaining contact of the knife edge bump 110 with the knurled attachment member 202.

In some luer connectors, the male luer 206 may have a rotating member 206. The female luer 204 may have a shape, for example, with flats or recesses, which interacts with the surface of the forked end 104 so as to keep it from rotating. Alternatively, or additionally, the size and shape of slot 120 may be chosen so as to grip an attached tube 212 from opposing sides. For example, the slot 120 may have a progressively narrowing shape. Portions indicated at 112 and 116 may stiffen the overall structure of the restraining clip 100.

Opposing surfaces of the opposite forked ends 104 may be provided with recesses into which the connector ends 204 and 206 fit. The size of the restraining clip 100 may be chosen such that an urging force is applied thereby forcing the connector ends 204, 206 together even when they are fully engaged. The photo of FIG. 8 shows how the restraining clip 100 can be deformed when in position to hold the connectors—in the illustrated example, luer connectors—together. The deformation can produce a restoring force that urges the parts together, even when the connectors are otherwise fully connected. The curved shape of the forked ends 104 also help to provide a force urging the knurls of attachment member 202 against knife edge bump 110 while the forked ends 104 are urged together by the restoring force of the restraining clip 100.

Figure 1:
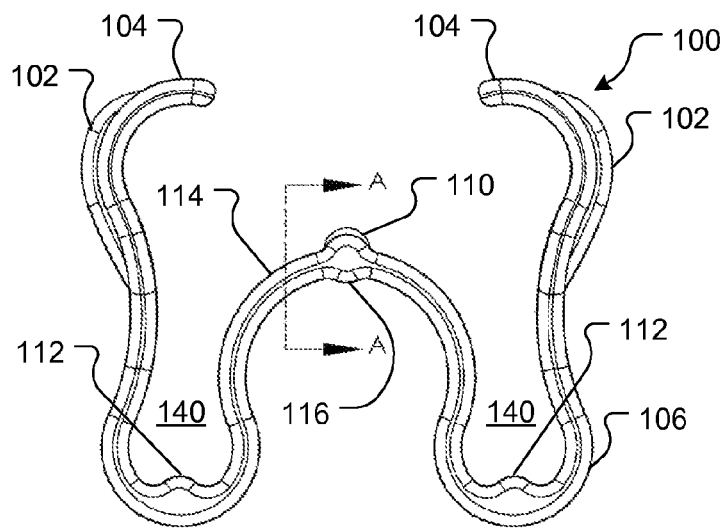
FIG. 1 is a side view of a restraining clip according to embodiments of the disclosed subject matter.
Figure 2:
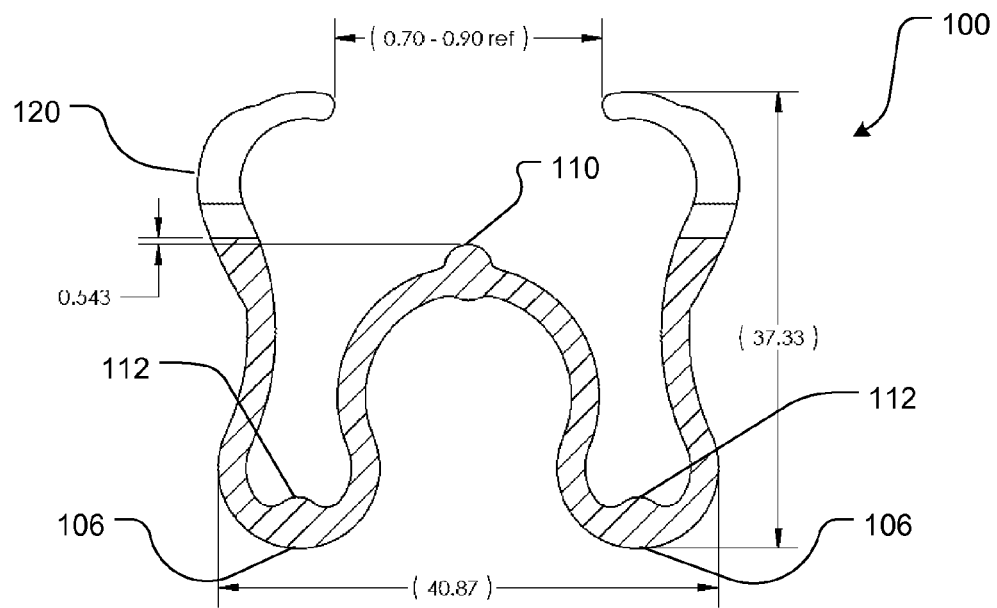
FIG. 2 is a section view C-C of the restraining clip taken along a plane parallel to the view of FIG. 1.
Figure 6:
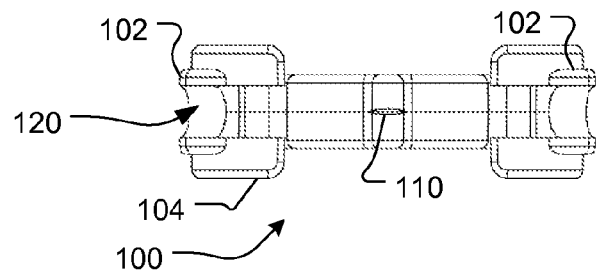
FIG. 6 is a plan view of the restraining clip of FIG. 1.

To use the restraining clip 100, the forked ends 104 are spread apart. This can be done with two hands or with one. For example, to apply the restraining clip 100 to a connection assembly using one hand, two fingers of the left or right hand are inserted into narrow loops 140 and squeezed together, thereby actuating the forked ends 104 away from each other. The restraining clip 100 is then placed into position about the connection assembly with each forked end 104 adjacent to a respective connector end of the connection assembly, at which time the narrow loops 140 are released. By virtue of the resiliency of the restraining clip 100, a biasing force is thus applied to the ends of the connectors of the connection assembly thereby urging the connectors together, as shown in FIG. 8. Exemplary dimensions for the restraining clip are shown in FIGS. 2, 4, and 5. However, such dimensions are for illustration purposes only and are not limiting of the sizes and shapes for embodiments of the restraining clip according to the present disclosure.

Figure 9:
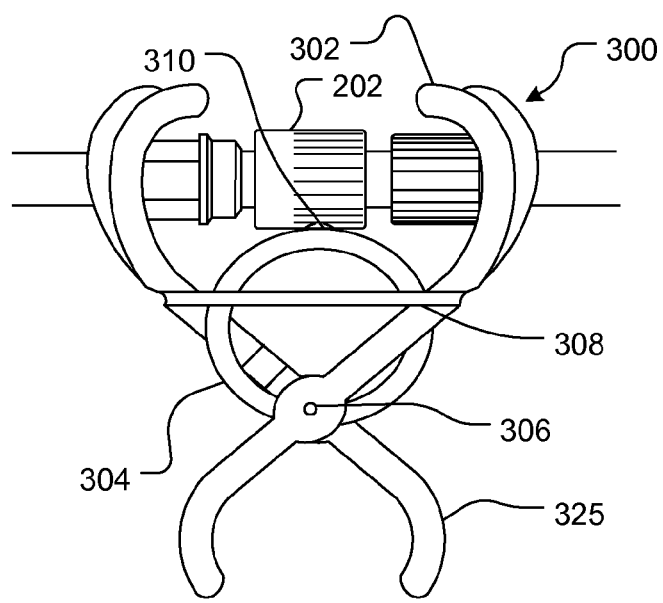
FIG. 9 shows a scissor-type restraining clip according to embodiments of the disclosed subject matter.
Figure 10:
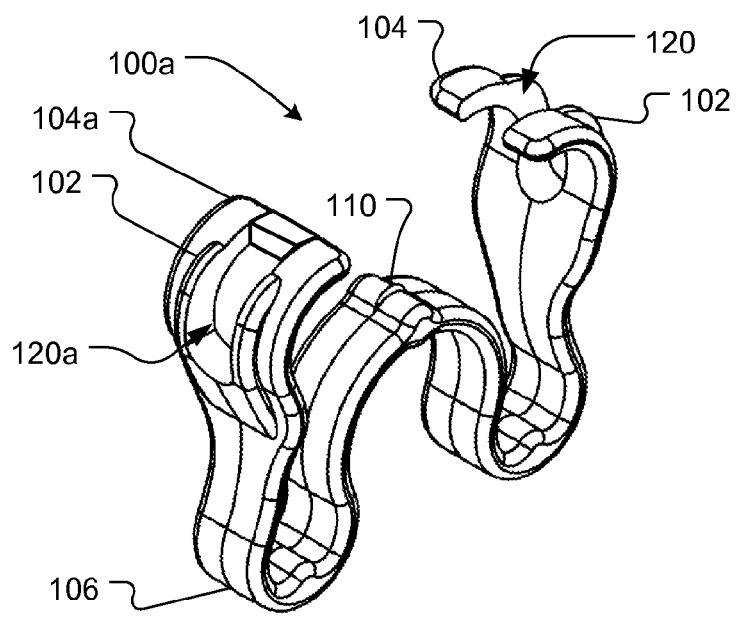
FIGS. 10 and 12 are oblique projection views of another restraining clip with a leash portion according to embodiments of the disclosed subject matter.
Figure 11:
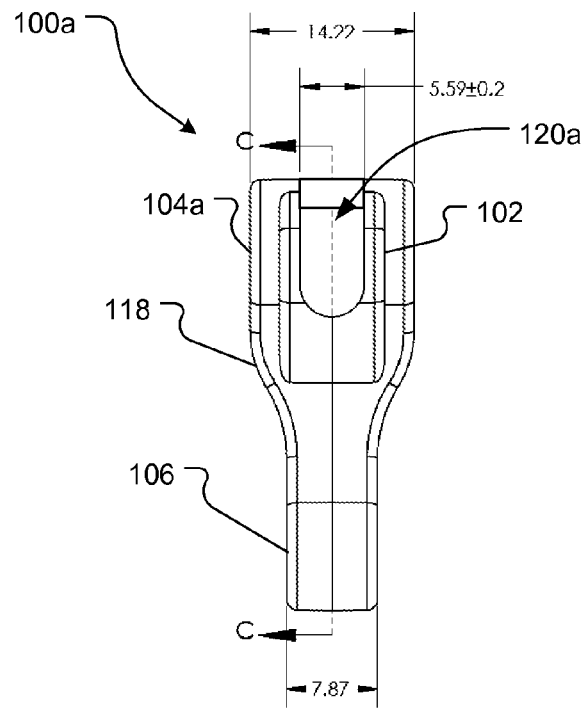
FIG. 11 is an end elevation view of the restraining clip of FIG. 10.
Figure 12:
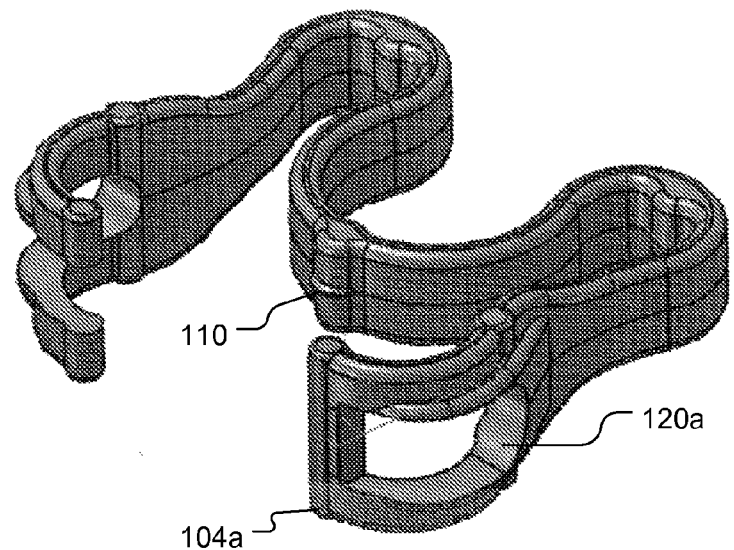
Figure 13:
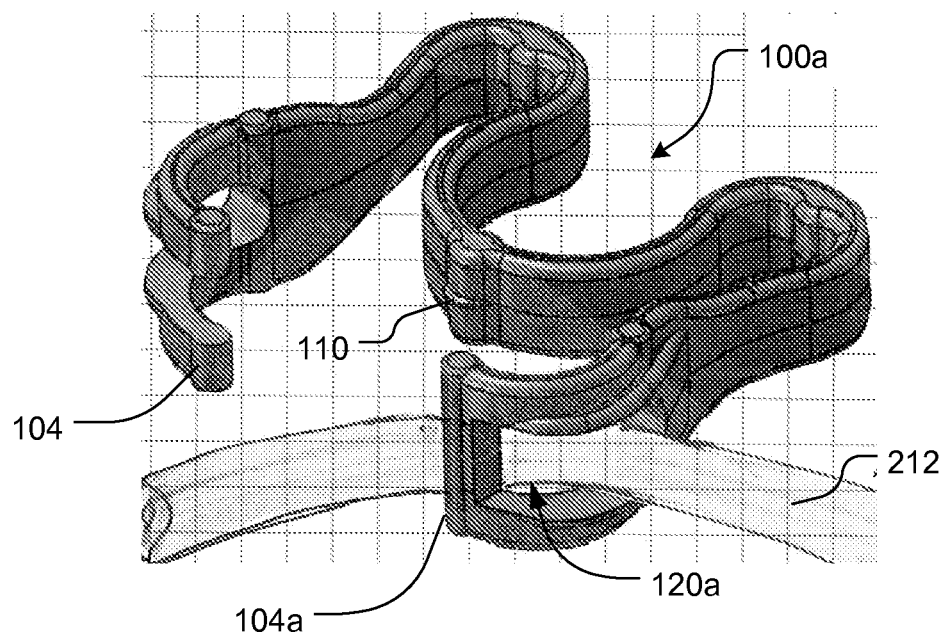
FIG. 13 is an oblique projection view of the restraining clip with leash portion of FIG. 11 installed on a tubing line, according to embodiments of the disclosed subject matter.

FIG. 9 shows an alternative embodiment 300 based on a scissor-type mechanism. An elastic band 308 generates a force to urge two curved forked ends 302 together. A knife edge bump 310 on a resiliently deformable circular member 304 is urged against the knurled male luer cap 202. The halves of the scissor mechanism and the circular member 304 are retained by a hinge pin 306. Handles 325 permit the device to be engaged and released with a single hand by pinching the handles 325 together.

In some applications, such as medical treatment applications, it may be desirable to use a new restraining clip for each new connection so as to insure reliability of the new connection that may otherwise be compromised by reuse of the restraining clip. To prevent reuse of the restraining clip, the restraining clip may be semi-permanently or permanently coupled with a single-use or disposable tubing line. Discarding the used tubing line would also discard the used restraining clip in favor of a new tubing line with a new restraining clip.

Referring to FIGS. 10-13, an alternative embodiment for a restraining clip according to the present disclosure is shown, which may be used in the above-described applications. Restraining clip 100a is similar to the restraining clip 100 illustrated in FIGS. 1-8; however, while one end 104 of restraining clip 100a retains the forked configuration with slot 120, the other end 104a has a closed opening 120a. For example, tines of one of the forked ends 104 in FIGS. 1-8 can be joined together by an attachment portion to enclose one end of opening 120a.

The recess 120a may be sized and shaped so as to accommodate a tubing line therethrough. The recess 120a may also be sized and shaped to prevent connector 204 (or 206) from passing therethrough. When installed on a tubing line 212, the connector 204 (or 206) would prevent the restraining clip 100a from being removed from the tubing line 212. To assemble the tubing line with the restraining clip, the tubing line 212 may be passed through opening 120a of the restraining clip 100a prior to installing the connector 204 (or 206) on the tubing line. End 104a thus forms a leash that attaches or secures the restraining clip 100a to one of the tubing lines 212, such that the restraining clip 100a can only be used with that tubing line. Replacement of the tubing line necessarily requires replacement of the restraining clip 100a. In an example, tubing line 212 is a blood tubing line for use in extracorporeal blood tubing sets.

Of course, other configurations for coupling the restraining clip to the tubing line such that both the tubing line and the restraining clip must be replaced together are also possible according to one or more contemplated embodiments. For example, the restraining clip could include a separate leash portion, either integrally formed as a part of the restraining clip or as a separate piece, which secures the restraining clip to a particular tubing line. In another example, the restraining clip leash portion may be formed as part of one of the connectors or permanently attached to one of the connectors of the connector assembly.

In any of the embodiments disclosed herein, the type of connector could be a luer-type connector or any other connector which relies on mutually rotatable parts on the connecting elements and/or which slide apart to disconnect. Also, although inline connectors are shown for purposes of illustration, the disconnect protection features shown can be applied to other types of connectors, such as, but not limited to connectors forming parts of junctions, components such as valves or filters, or others.

Features of the disclosed embodiments may be combined, rearranged, omitted, etc., within the scope of the present disclosure to produce additional embodiments. Furthermore, certain features may sometimes be used to advantage without a corresponding use of other features.

It is, thus, apparent that there is provided, in accordance with the present disclosure, fluid line safety devices, mechanisms, and methods. Many alternatives, modifications, and variations are enabled by the present disclosure. While specific embodiments have been shown and described in detail to illustrate the application of the principles of the invention, it will be understood that the invention may be embodied otherwise without departing from such principles. Accordingly, Applicants intend to embrace all such alternatives, modifications, equivalents, and variations that are within the spirit and scope of the present invention.

The invention claimed is:

1. A restraining device, comprising:
a resilient member having a generally U-shape with forked ends that curve toward each other;
each forked end having a recess between tines thereof, each recess having a blind end;
a bend in the resilient member being provided with an engagement bump;
the engagement bump and forked ends being aligned such that the engagement bump coincides with a line joining the blind ends, the engagement bump being provided on a U-shaped portion that is opposite and in the middle of the general U-shape of the resilient member;
wherein, when a cylindrical connector assembly tube is placed in the recesses, the engagement bump is urged against a side of the connector assembly.

2. The device of claim 1, wherein the resilient member is made of a polymer.

3. The restraining device of claim 1, wherein the engagement bump is on a bowl of the U-shape, and the bump-bearing bowl bends toward the line joining the blind ends forming a W-shape.

4. A restraining member for a connector assembly comprising:
a forked first end having a first recess between tines thereof, the first recess being sized and shaped so as to accept a first tubing connected to one end of the connector assembly;
a closed second end having an opening therein, the second end being sized and shaped so as to accept a second tubing connected to an other end of the connector assembly; and
a bend with an engagement bump arranged between the first and second ends,
wherein the bend is arranged such that, when the first and second ends abut against respective first and second ends of the connector assembly, the first and second ends engaging by threading one into the other and the engagement bump interferingly engaging with a knurled attachment member of one of the first and second ends so as to prevent rotation thereof.

5. The restraining member of claim 4, wherein the member is made of a polymer.

6. A tubing set comprising:
a restraining member having a U-shaped configuration with a middle bend end risers including:
a forked first end on a first of the risers having a first recess between tines thereof;
a closed second end on a second of the risers having an opening therein; and
the middle bend having an engagement bump arranged on the middle bend between the first and second ends;
a tubing line passing through the opening in the closed second end of the restraining member; and a connector attached to an end of said tubing line;

the engagement bump being positioned to interfering engage with a first connector attached to the tubing line or a second connector adapted for threadingly connecting with the first connector.

7. The tubing set of claim 6, wherein the connector is one of a male luer-type connector and a female luer-type connector.

8. The tubing set of claim 6, wherein the tubing line is a blood tubing line.

9. The tubing set of claim 6, wherein the engagement bump is on a bowl of the U-shape, and the bump-bearing bowl bends toward a line joining blind ends forming a W-shape.

* * * * *